(12) United States Patent
Zimmermann

(10) Patent No.: US 7,945,455 B2
(45) Date of Patent: May 17, 2011

(54) PHARMACEUTICAL DISTRIBUTION SYSTEMS AND METHODS

(75) Inventor: Halden Zimmermann, Dublin, OH (US)

(73) Assignee: Cardinal Health Technologies, LLC, Las Vegas, NV (US)

( * ) Notice: Subject to any disclaimer, the term of this patent is extended or adjusted under 35 U.S.C. 154(b) by 511 days.

(21) Appl. No.: 12/022,873

(22) Filed: Jan. 30, 2008

(65) Prior Publication Data

US 2009/0192819 A1 Jul. 30, 2009

(51) Int. Cl.
*G06Q 10/00* (2006.01)
*G06Q 50/00* (2006.01)

(52) U.S. Cl. .......................................................... 705/2

(58) Field of Classification Search .................. None
See application file for complete search history.

(56) References Cited

U.S. PATENT DOCUMENTS

| | | | |
|---|---|---|---|
| 5,593,267 A * | 1/1997 | McDonald et al. ............ 414/273 |
| 5,641,093 A * | 6/1997 | Dolin et al. .................... 221/282 |
| 6,112,502 A * | 9/2000 | Frederick et al. ............... 53/411 |
| 6,219,587 B1 * | 4/2001 | Ahlin et al. .................... 700/233 |
| 6,814,535 B1 | 11/2004 | Maness |
| 7,171,377 B2 | 1/2007 | Ogasawara |
| 7,518,516 B2 * | 4/2009 | Azevedo et al. ............ 340/572.1 |
| 2003/0105552 A1 * | 6/2003 | Lunak et al. ................... 700/214 |
| 2004/0111179 A1 * | 6/2004 | Broadfield et al. ............ 700/214 |
| 2004/0158507 A1 * | 8/2004 | Meek et al. ...................... 705/28 |
| 2005/0043850 A1 | 2/2005 | Stevens et al. |
| 2007/0250346 A1 * | 10/2007 | Luciano et al. ................... 705/2 |
| 2009/0108016 A1 * | 4/2009 | Brown et al. .................... 221/28 |

FOREIGN PATENT DOCUMENTS

JP 2003095439 A * 4/2003

* cited by examiner

*Primary Examiner* — Gerald J. O'Connor
*Assistant Examiner* — Sheetal R Rangrej
(74) *Attorney, Agent, or Firm* — Arent Fox LLP

(57) ABSTRACT

A method of distributing pharmaceutical items from a primary distributor to a secondary seller. A request for pharmaceutical items is received by the primary distributor from the secondary seller. Shelving information indicative of a sequential arrangement of pharmaceutical items along the secondary seller's shelving system is reviewed. A mobile cart having a plurality of compartments is provided, and a sequential order to the plurality of compartments is designated. Based upon the request, the shelving information, and the compartment order, a compartment assignment plan is generated that assigns the requested pharmaceutical items to respective compartments in an order corresponding with the sequential arrangement of the shelving system. The compartments are then loaded in accordance with the compartment assignment plan, and delivered to the secondary seller.

24 Claims, 9 Drawing Sheets

| COMPARTMENT ASSIGNMENT PLAN | | | | |
|---|---|---|---|---|
| P1 $C_{1,1}$ | P12 $C_{1,2}$ | $C_{1,3}$ | $C_{1,4}$ | |
| P1 $C_{2,1}$ | P17 $C_{2,2}$ | $C_{2,3}$ | $C_{2,4}$ | |
| P1 $C_{3,1}$ | P17 $C_{3,2}$ | $C_{3,3}$ | $C_{3,4}$ | |
| P5 $C_{4,1}$ | P17 $C_{4,2}$ | $C_{4,3}$ | $C_{4,4}$ | |
| P5 $C_{5,1}$ | $C_{5,2}$ | $C_{5,3}$ | $C_{5,4}$ | |

COMPARTMENT ASSIGNMENT PLAN

| | | | | |
|---|---|---|---|---|
| P1<br>$C_{1,1}$ | P1<br>$C_{2,1}$ | P1<br>$C_{3,1}$ | P5<br>$C_{4,1}$ | P5<br>$C_{5,1}$ |
| P12<br>$C_{1,2}$ | P17<br>$C_{2,2}$ | P17<br>$C_{3,2}$ | P17<br>$C_{4,2}$ | P32<br>$C_{5,2}$ |
| P32<br>$C_{1,3}$ | P32<br>$C_{2,3}$ | P25<br>$C_{3,3}$ | $C_{4,3}$ | $C_{5,3}$ |
| $C_{1,4}$ | $C_{2,4}$ | $C_{3,4}$ | $C_{4,4}$ | $C_{5,4}$ |

PHARMACEUTICAL DISTRIBUTION SYSTEMS AND METHODS

BACKGROUND

The present disclosure relates to systems and methods for distributing pharmaceuticals. More particularly it relates to systems, methods, and related devices for preparing and shipping an inventory of different, pre-packaged pharmaceutical items (e.g., prescription and non-prescription medications) from a primary distributor to a secondary seller of the items, such as a retail pharmacy or a mail-order pharmacy.

Primary distributors or distribution centers commonly facilitate distribution of pharmaceutical items from a manufacturer to a secondary seller ("retail seller"). By way of background, a typical pharmaceutical distribution methodology entails the primary distributor warehousing significant quantities of a large number of different, pre-packaged medications or other pharmaceutical items made by various manufacturers. Retail sellers ultimately sell at least some of these items to patients, and thus desire to have a small amount of a number of medications on-hand (or in stock) at all times. It will be understood that the number of manufacturers involved and the relatively small quantities needed render it highly impractical for a retailer seller to order directly from a manufacturer. Thus, the retail seller periodically orders various quantities of some of the pre-packaged pharmaceutical items offered by the primary distributor in volumes commensurate with actual or expected sales. In this regard, retail sellers commonly maintain their in-house stock or small inventory of packaged pharmaceutical items at an on-site shelving system, consistently storing the particular medications/formats on the shelves in a designated, retail seller-specific order.

While retail sellers may sell more of some medications as compared to others, pharmaceutical item orders placed with the primary distributor essentially always include a number of different pharmaceutical types, as well as different formats (e.g., a single order from a retail seller to a primary distributor can include twenty packages of medication product A in 100 mg tablet form, forty packages of medication product A in 500 mg capsule form, thirty packages of medication product B, twenty-five packages of medication product C, etc.). As a point of reference, certain retail sellers (e.g., mail-order pharmacies) may fill in upwards of 20,000 prescriptions per day, and thus will order significant quantities from the primary distributor. Regardless, upon receiving an order, employees of the primary distributor "fill" the order by preparing one or more boxes or "totes" with requested quantities of each pharmaceutical item/format. The totes are typically of a standard size and can hold a fairly large number of individual, packaged pharmaceutical items. For many retail sellers, however, a single tote is not large enough to hold all ordered products. Under these circumstances, the primary distributor will prepare or fill a series of totes to meet the retail seller's order. Some of the totes may contain only a single type of medication; others will contain a plurality of different pharmaceuticals/formats. The filled totes are banded to a skid and then shipped to the retail seller.

For certain retail sellers, the primary distributor will have a general understanding of the designated areas or order the retail seller stores its on-site supply of pharmaceuticals, and thus will attempt to generally organize/label the totes in accordance with the expected shelving location. For example, the retail seller may have three lines or rows of shelves, with pharmaceutical items A-F stored in the first line of shelves; pharmaceutical items G-N stored in the second line of shelves; and pharmaceutical items P-Z stored in the third line of shelves. Under these circumstances, the primary distributor will endeavor to place pharmaceutical items A-F in a series of totes that are each labeled "Shelves 1" (or similar designation); pharmaceutical items G-N in one or more totes each labeled "Shelves 2"; and pharmaceutical items P-Z in one or a series of totes each labeled "Shelves 3".

Regardless of whether the totes are loaded in accordance with general shelving designations assigned by the retail seller, upon receiving a shipment from the primary distributor, the retail seller's employees must un-band the totes from the skid, open each tote to confirm content, and then remove all packaged pharmaceuticals from the totes. The removed packaged products are then placed on an open, wheeled cart in a somewhat ordered fashion. More particularly, the retail seller's employee will likely be aware of the pre-designated ordering of pharmaceutical products along the retail seller's shelving system. With this in mind, the employee may attempt to load the individual, packaged pharmaceutical items onto the open cart in a manner generally corresponding with the shelving system order. For example, all medication products stored in the first line of shelves are placed onto one cart, all medication products stored in the second line of shelves are placed onto a second cart, etc. From this point, the retail seller's employee wheels the cart along the designated line of shelves, removing pharmaceutical items from the cart and placing them at appropriate locations along the shelving system. This can be a time consuming task as the items are often randomly arranged on the cart, requiring the worker to repeatedly move back-and-forth along the shelves.

While widely used, the current methodologies for distributing pharmaceuticals from a primary distributor to a retail seller (especially a high volume retail seller, such as a mail order pharmacy) necessitate that the packaged pharmaceuticals be handled several times, and require that the retail seller perform a number of processing steps. The time required for the retail seller's employees to unload the shipped pallet and then re-load individual carts may lead to undesirable stock out issues. Further, the emptied totes are accumulated at the retail seller's site, and must be returned to the primary distributor.

SUMMARY

Some aspects in accordance with principles of the present disclosure relate to a method of distributing pharmaceutical items from a primary distributor to a secondary seller of pharmaceuticals. The method includes maintaining an inventory pharmaceutical items at the primary distributor. A request for a plurality of differing pharmaceutical items is received by the primary distributor from the secondary seller. Shelving information indicative of a sequential arrangement of pharmaceutical items along a shelving system maintained by the secondary seller is reviewed. A mobile cart having a plurality of compartments is provided, and a sequential order of the plurality of compartments is designated. Based upon the request, the shelving information, and the designated sequential order of compartments, a compartment assignment plan is created that assigns the requested pharmaceutical items to respective compartments in an order corresponding with the sequential arrangements of the shelving system. The compartments are then loaded with the requested pharmaceutical items from the primary distributor's inventory in accordance with the compartment assignment plan. The so-loaded cart is delivered to the secondary seller. In some embodiments, the secondary seller unloads the pharmaceutical items directly from the cart to the shelving system, such as by rolling the cart in a single direction along a line of shelves.

BRIEF DESCRIPTION OF THE DRAWINGS

FIG. 6 is an example Component Assignment Plan generated in accordance with principles of the present disclosure;

FIG. 8 is another example Compartment Assignment Plan generated in accordance with principles of the present disclosure.

DETAILED DESCRIPTION

Figure 1:
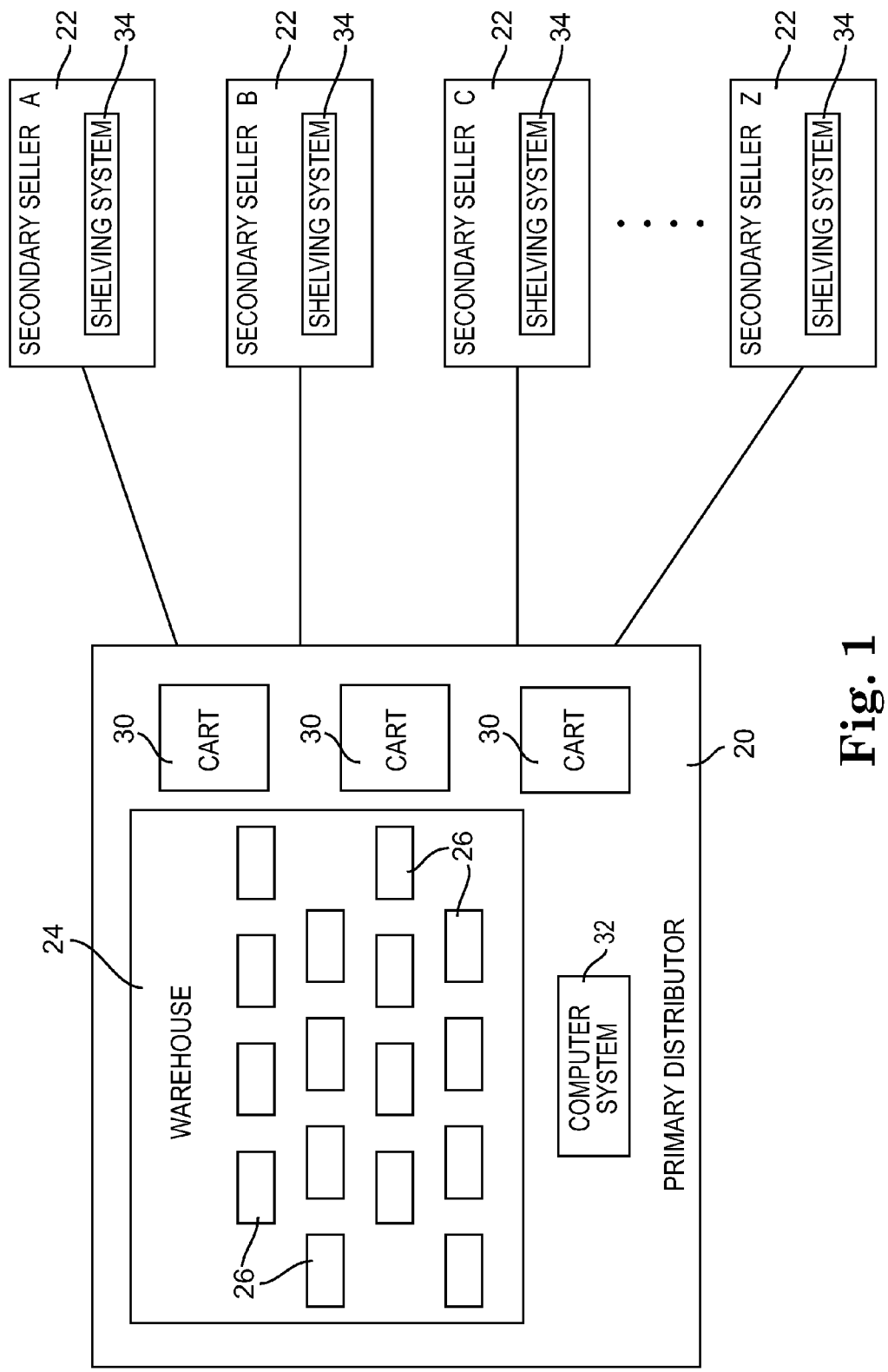
FIG. 1 is a block diagram of a pharmaceutical distribution system, including components useful with systems and methods in accordance with principles of the present disclosure.

Aspects of the present disclosure relate to systems and methods for distributing pharmaceutical items from a primary distributor 20 to one or more secondary sellers 22 as generally reflected by the block diagram of FIG. 1. The primary distributor 20 (for example a pharmaceutical distribution center) operates one or more warehouses 24 at which a large inventory of a plurality of different pharmaceutical items 26 (referenced generally) are maintained. With this in mind, systems and methods in accordance with the present disclosure include one or more mobile (e.g., wheeled) carts 30 and a computer system 32. The carts 30 are described in greater detail below. In general terms, however, in response to a request or order for pharmaceutical items from one of the secondary sellers 22, the computer system 32 operates to generate a plan for loading one or more of the carts 30 with requested quantities of the pharmaceutical item(s) 26 for delivery to the secondary seller 22. In this regard, the plan dictates loading of the cart(s) 30 in a manner that facilitates direct, convenient unloading of the delivered pharmaceutical items 26 along a shelving system 34 utilized at or by the secondary seller 22 being served.

Figure 2:
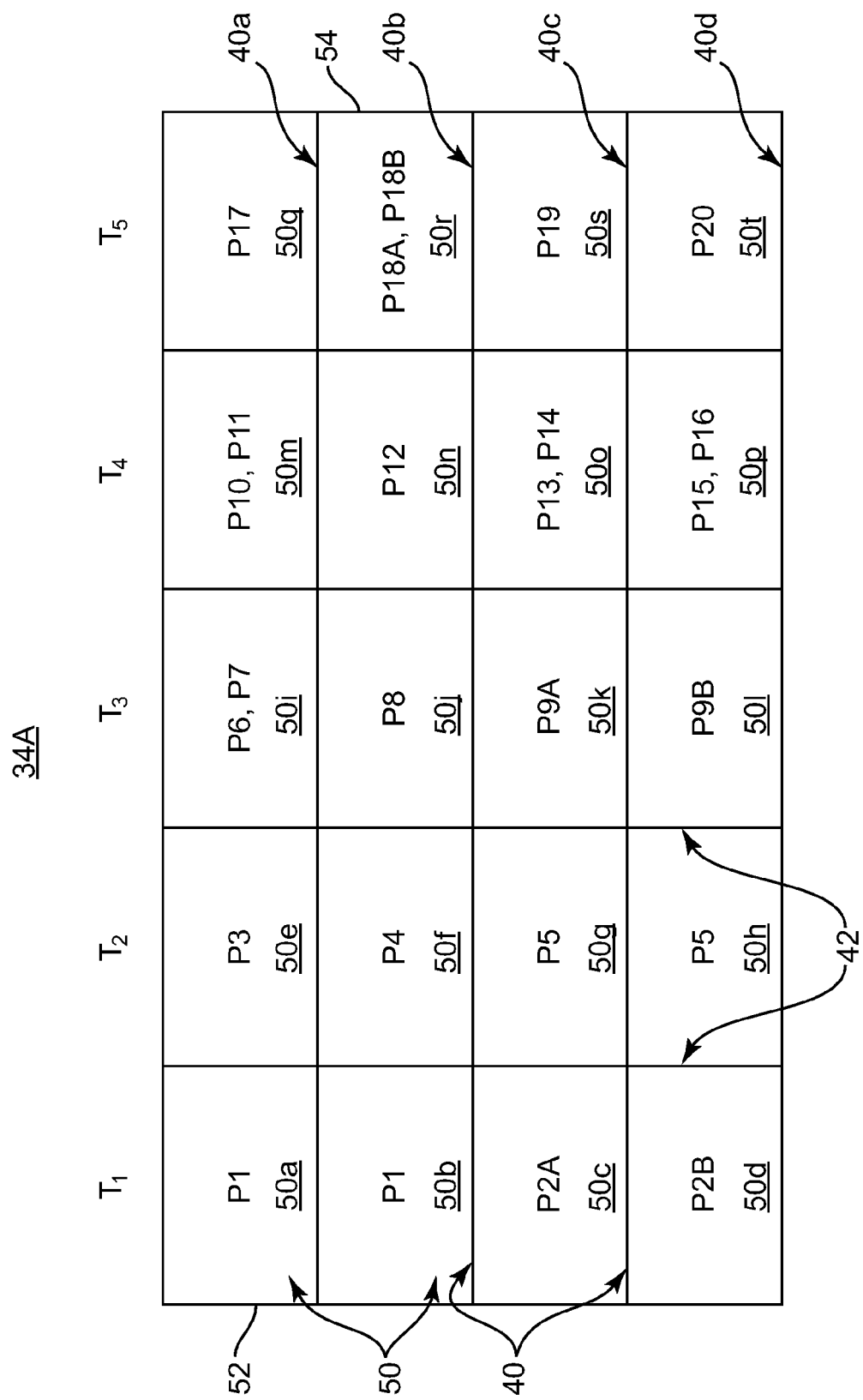
FIG. 2 is a simplified side view of an example shelving system useful by a secondary seller of the distribution system of FIG. 1.

As a point of reference, each of the secondary sellers 22 can employ a differing shelving system 34. The differences can be characterized by the number of shelves, the arrangement of shelves, etc. Further, even where the physical shelves are identical between two different secondary sellers 22, the arrangement of pharmaceutical items 26 along those shelves is unique. For example, FIG. 2 is a simplified illustration of one possible shelving system 34A. The shelving system 34A includes shelves 40 and dividers 42. The shelves 40 are arranged vertically relative to one another and can include, for example, a first or top shelf 40a, the second shelf 40b, and a third shelf 40c. A floor 40d of the shelving system 34 can also serve as a shelf. A variety of framing components or walls can be employed to retain the shelves 40a-40d relative to one another; similarly more or less of the shelves 40a-40d can be provided. In addition, typically for load bearing support, the shelving system 34 includes the vertically extending dividers 42. With the one configuration of FIG. 2, four of the dividers 42 are provided that serve to divide the shelving system 34 into five vertical segments $T_1$-$T_5$, it being understood that more or less can also be employed. Regardless, the shelves 40 and the dividers 42 (and possibly other shelving structures) partition the shelving system 34 into a plurality of storage regions 50.

The secondary seller 22 typically incorporates the above-described, conventional attributes of the shelving system 34 in maintaining a small supply or inventory of various pharmaceutical items in a relatively organized fashion. More particularly, specific pharmaceutical items are always stored in the same region or regions 50 so as to be more quickly located when needed. Thus, for example, FIG. 2 reflects the shelving system 34A as having or defining twenty of the storage regions $50a$-$50t$. The shelving system 34A can conventionally be viewed as defining a first end 52 and a second end 54, with either end 52 or 54 serving as the "front" or entrance end and the other as the "back" or exit end (i.e., when conventionally considered in a left-to-right fashion, the first end 52 serves as a front or entrance, and the second end 54 serves as a back or exit).

A further conventional approach for designating the various storage regions $50a$-$50t$ within each segment $T_1$-$T_5$ is in a top-to-bottom manner. Thus, the upper left-most storage region $50a$ can be viewed as being the "first" storage region of the shelving system 34A, whereas the lower right-most storage region $50t$ can be viewed as being the "last" storage region. Following these conventions, then, different types/formats of the pharmaceutical items 26 can be consistently stored in a selected one (or more) of the storage regions $50a$-$50t$. For example, FIG. 2 reflects that a quantity of a first type of pharmaceutical item ("P1") is always stored in the first and second storage regions $50a$, $50b$. The third storage region $50c$ is designated or assigned for placement of a second type of pharmaceutical item in a first format ("P2A"), whereas the fourth storage region $50d$ is designated for the second type of pharmaceutical item in a second format ("P2B"). Additional, example pharmaceutical item/storage region 50 designations are further reflected in FIG. 2 for illustration purposes only, it being understood that this is but one acceptable arrangement of pharmaceutical items along the shelving system 34A as done by a particular secondary seller 22.

Figure 3:
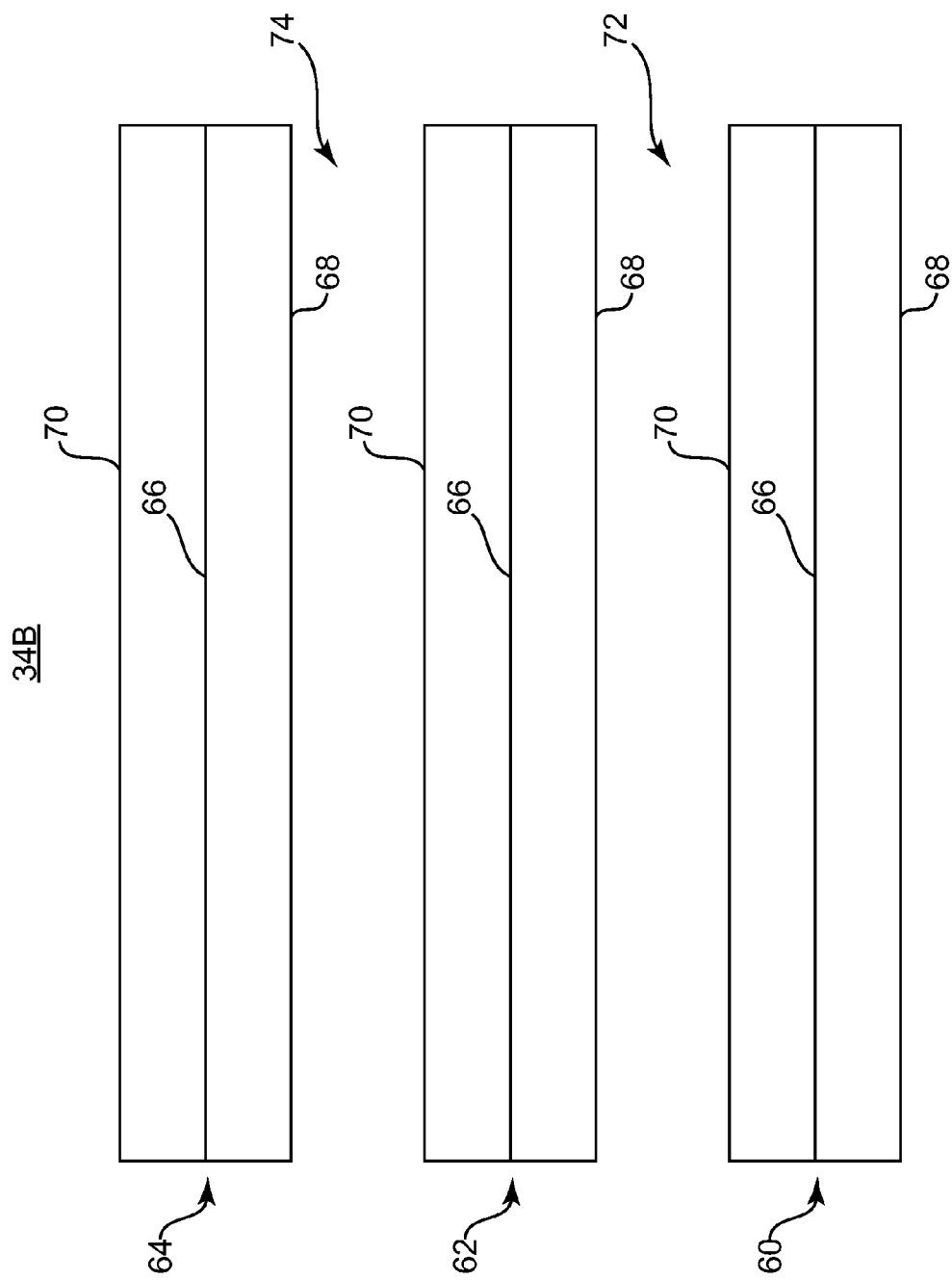
FIG. 3 is a simplified top view of another example shelving system useful by a secondary seller of the distribution system of FIG. 1.

While the shelving system 34A of FIG. 2 includes a single line of shelves, other shelving systems 34 employed by one or more of the secondary sellers 22 (FIG. 1) can include two or more lines of shelves arranged side-by-side. For example, FIG. 3 is a simplified top view of another shelving system 34B including a first line of shelves 60, a second line of shelves 62, and a third line of shelves 64. Each one of the lines of shelves 60-64 can be akin to the shelving system 34A of FIG. 2, and thus provides a series or array of storage regions (not shown in FIG. 3). Further, each line of shelves 60-64 can include a central partition 66 (referenced generally) such that discrete storage regions are available or accessible at both sides 68, 70 of each of the lines of shelves 60-64. With the side-by-side arrangement, then, the first and second lines of shelves 60, 62 are separated by a first aisle 72, whereas the second and third lines of shelves 62, 64 are separated by a second aisle 74. A person located along the first aisle 72 can access the storage regions of the second side 70 of the first line of shelves 60 as well as storage regions of the first side 68 of the second line of shelves 62. The second aisle 74 provides the same accessibility relative to the storage regions of the second side 70 of the second line of shelves 62 and the first side 68 of the first line of shelves 60.

As should be clear from the above, shelving systems employed by the secondary sellers 22 can assume a wide variety of configurations. In most basic terms, however, the shelving system 34 and related arrangement of pharmaceutical items 26 utilized by each secondary seller 22 presents specific pharmaceutical items at specific locations. The systems and methods of the present disclosure incorporate or make use of the organizational arrangement of each secondary seller's shelving system when loading a cart(s) with requested pharmaceutical items.

Figure 4:
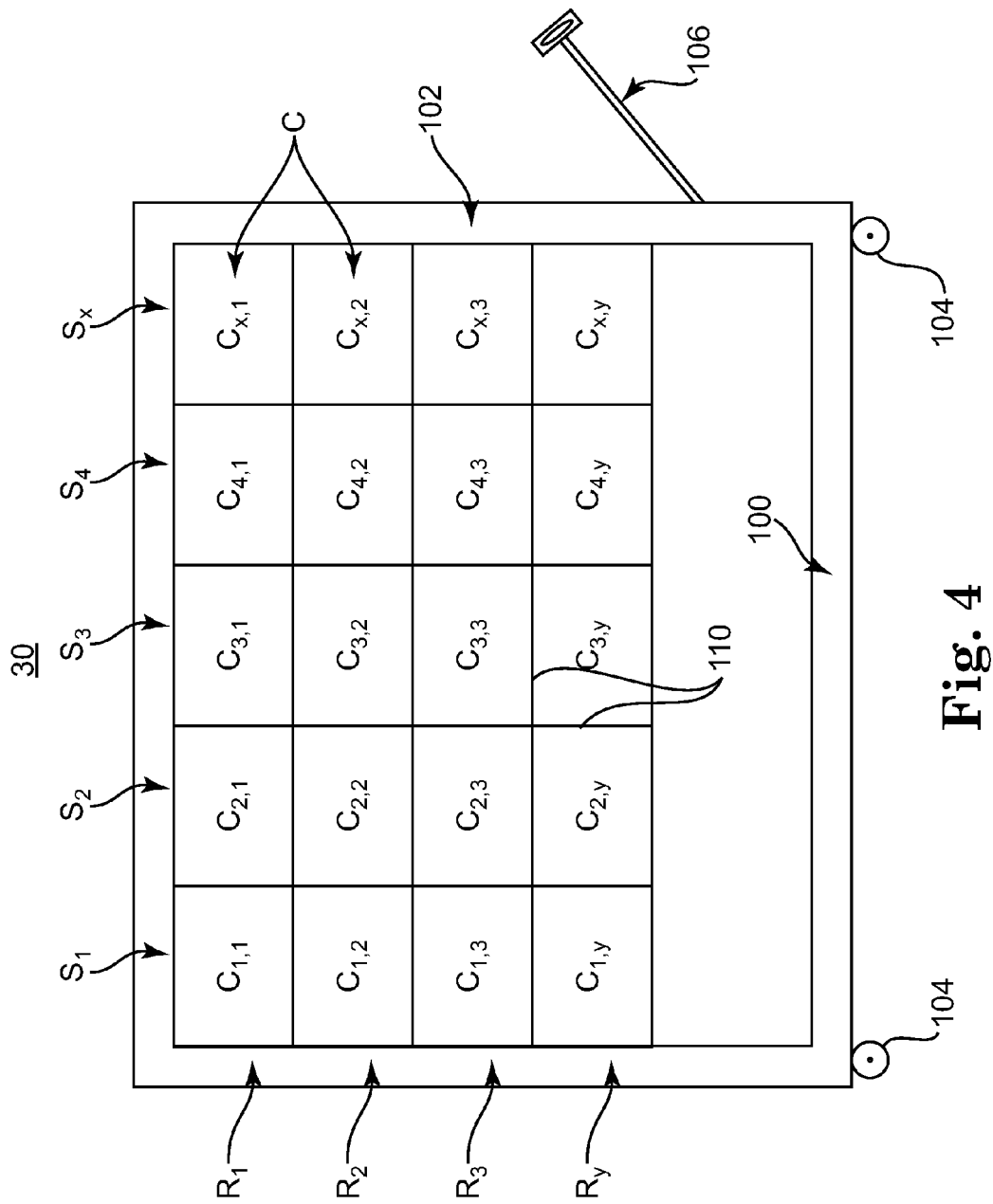
FIG. 4 is a simplified side view of a cart useful with the distribution systems and methods of the present disclosure.

For example, FIG. 4 is a simplified view of a cart 30 useful with the present disclosure. The cart 30 can assume a wide variety of forms, and generally includes a base 100 maintaining framework 102 and wheels 104 (or other components that render the card 30 mobile). The framework 102 forms or defines a plurality of compartments C as described below for temporarily storing pharmaceutical items (not shown). The wheels 104 render the cart 30 movable along a flat surface, with the cart 30 including a handle 106 or other feature(s) that promote movement of the cart 30 by a user.

With the general construction of the cart 30 in mind, the compartments C are arranged in an array format, defining a series of individual, discrete storage areas. In this regard, the framework 102 can include a variety of different structures (e.g., walls 110) that separate the compartments C from one another. Regardless, with the array configuration, the compartments C can be viewed as being arranged in a plurality of rows R of aligned, sequentially positioned compartments. For example, FIG. 4 illustrates the framework 102 as establishing a top or first row $R_1$ of compartments C. A second row $R_2$ of the compartments C is arranged below the top row $R_1$, and a third row $R_3$ positioned below the second row $R_2$. A bottommost row of the compartments C is labeled as $R_y$ in FIG. 4 to reflect that any number of rows R can be provided. Thus, the cart 30 can have three or less, or five or more of the vertically arranged rows R of compartments C. Further, while the compartments C associated with each of the rows $R_1$-$R_y$ are illustrated as being generally identical in size, with other configurations, a size of the compartments C can vary from row-to-row and/or within each of the individual rows R. Consistent with this arrayed description, the compartments C can further be designated as being arranged in horizontal columns or series designated as $S_1$-$S_x$ in FIG. 4.

With the above conventions in mind, the top row $R_1$ can be viewed as arranging the corresponding compartments C in a left-to-right manner relative to the sequential columns S. Thus, the first row $R_1$ includes a first compartment $C_{1,1}$ at the upper left corner of the framework 102. A second compartment $C_{2,1}$ is provided to the right of the first compartment $C_{1,1}$, followed by a third compartment $C_{3,1}$, etc. The number of compartments C in the first row $R_1$ can vary depending upon the particular cart configuration; thus in FIG. 4, the last compartment C in the first row $R_1$ is designated as $C_{x,1}$. The compartments C of the second row $R_2$ can be directly aligned with corresponding ones of the compartments C of the first row $R_1$ as shown, or can be off-set relative thereto. Regardless, the compartments C of the second row $R_2$ can be designated as sequentially arranged in a left-to-right manner, beginning with a first compartment $C_{1,2}$, followed by a second compartment $C_{2,2}$, etc. Once again, any number of compartments C can be provided with the second row $R_2$, with FIG. 4 designating the last compartment of the second row $R_2$ as compartment $C_{x,2}$. A similar designation (left-to-right) of the compartments C provided with the third row $R_3$ is further provided in FIG. 4, along with designators for the hypothetical bottom row $R_y$, with the compartment C at the lower-right corner designated as $C_{x,y}$.

The cart 30 as described above with respect to FIG. 4 is but one example of a configuration useful with the systems and methods of the present disclosure. Optional modifications and/or additional features are described below. Further, and returning to FIG. 1, the primary distributor 20 may have a plurality of identically-constructed carts available for distributing pharmaceutical items to various ones of the secondary sellers 22, or can have carts with different constructions (i.e., different numbers or arrangement of compartments). Regardless, the arrangement of the cart's compartments C (FIG. 4) is correlated with the arrangement of pharmaceutical items along the secondary seller's shelving system 34 in devising an optimal loading plan for the cart(s) 30 being delivered to the secondary seller.

Figure 5:
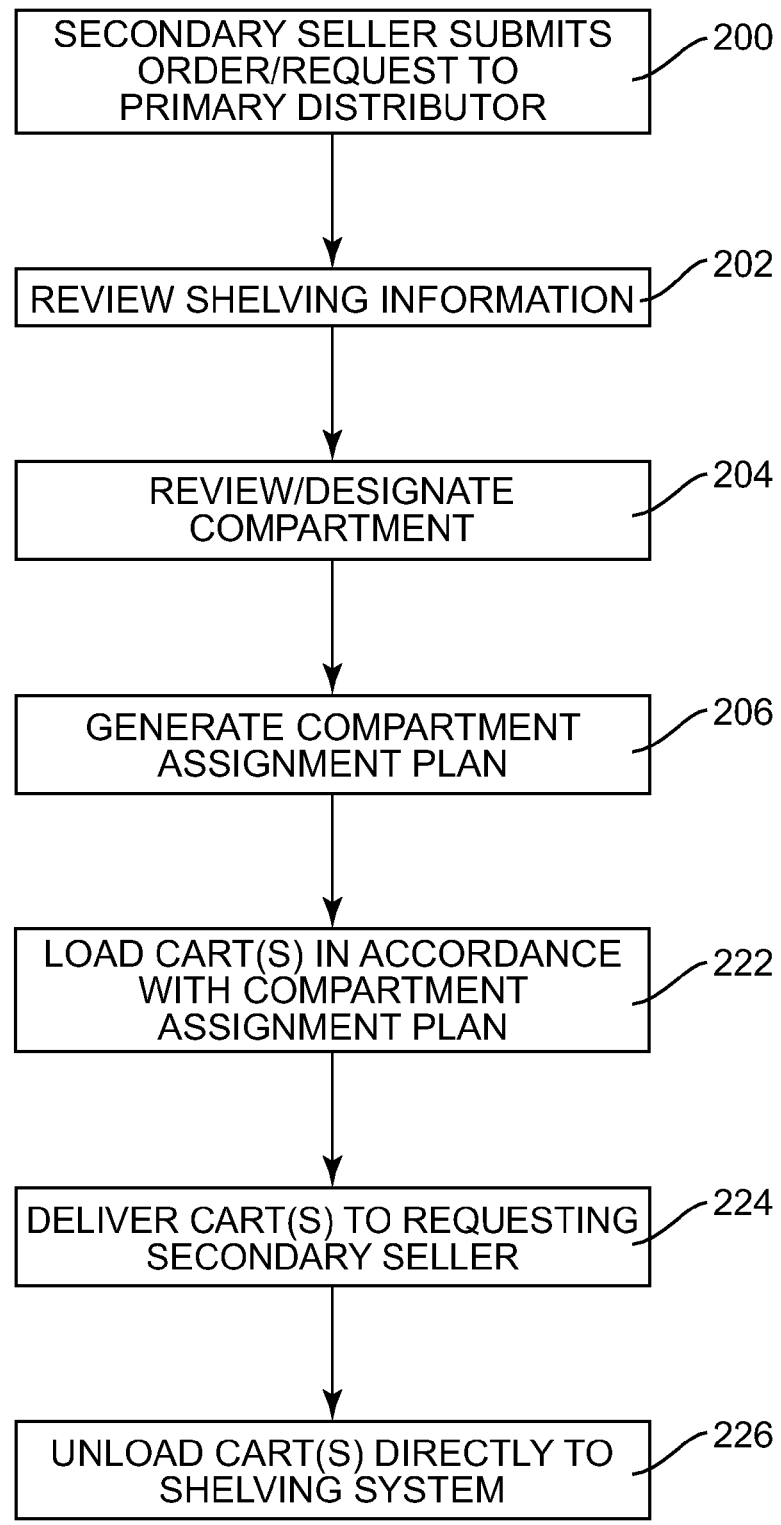
FIG. 5 is a flow diagram illustrating a method of distributing pharmaceutical items in accordance with principles of the present disclosure.

More particularly, systems and methods of the present disclosure facilitate streamlined delivery of pharmaceutical items from the primary distributor 20 to the secondary seller 22 requesting (ordering) items from the primary distributor 20 by generating a Compartment Assignment Plan for loading one or more of the carts 30 in a manner corresponding with the order in which pharmaceutical items are maintained by the secondary seller 22 along its shelving system. With additional reference to FIG. 5, the distribution process begins at step 200 when the primary distributor 20 receives a request from one of the secondary seller 22 ("the requesting secondary seller") for various pharmaceutical items. The request can be delivered in any conventional format (electronic purchase order, phone, mail, etc.), and will include the number/quantity and type of each pharmaceutical item desired.

In response to the request or order, at step 202 the computer system 32 is operated by the primary distributor 20 to review shelving information indicative of a sequential arrangement of pharmaceutical items along the requesting secondary seller's 22 particular shelving system 34. As a point of reference, the shelving information will typically include the locations (relative to requesting secondary seller's shelving system 34) of all pharmaceutical item(s) maintained by the requesting secondary seller, and thus will include location information for pharmaceutical items that are not otherwise part of the particular request being processed by the primary distributor 20. The shelving information can be delivered or provided to the primary distributor 20 by the secondary seller 22 as part of the request at step 200. Alternatively, the computer system 32 can maintain an electronic database or library in which the shelving information for a plurality of different secondary sellers 22 is maintained and can be reviewed by the computer system 32 upon receiving a request from a particular secondary seller. Even further, the shelving information can be generated/updated over time by the primary distributor 20 and/or the secondary seller 22 (and possibly stored by the computer system 32). In more general terms, the shelving information includes the requesting secondary seller's pharmaceutical item arrangement as described above, for example with respect to FIGS. 2 and 3.

The computer system 32 also reviews, at step 204, the number and arrangement of compartments provided with a particular cart (or carts) that will otherwise be used to deliver the requested pharmaceutical items to the requesting secondary seller 22. As described above with respect to FIG. 4, the cart(s) 30 available to the primary distributor 20 will have a known arrangement (i.e., location and number) of the compartments C. This compartment information can be stored in a database maintained by the computer system 32 and/or can be entered by a user. Further, the compartment information available to the computer system 32 can include additional details, such as a size or volume of one or more or all of the compartments C of a selected cart(s) 30.

With the requested items, shelving information, and compartment information in hand, the computer system 32 generates a Compartment Assignment Plan at step 206 in which specific pharmaceutical items are assigned to particular ones of the compartments C of the selected cart(s). The Compartment Assignment Plan correlates the expected order in which the requested pharmaceutical items will be distributed along the requesting secondary seller's shelving system 34 with the sequential ordering of the compartments C. In this regard, the computer system 32 designates a sequential ordering to the compartments C and assigns pharmaceutical items in accordance with this designation. Generation of one Compartment Assignment Plan is illustrated by the following example.

For purposes of this example, it is assumed that the requesting secondary seller's shelving system 34 and arrangement of pharmaceutical items has the form of FIG. 2. Further, it is assumed that the cart 30 selected by the primary distributor is akin to that of FIG. 4, and includes four rows of five compartments C. Finally, for purposes of this but one example, a request is received by the primary distributor 20 from the requesting secondary seller 22 for a quantity of the first pharmaceutical item P1, a quantity of the fifth pharmaceutical item P5, a quantity of the twelfth pharmaceutical item P12, and a quantity of the seventeenth pharmaceutical item P17. Notably, the actual request delivered to the primary distributor 20 may or may not list the requested pharmaceutical items P in the same sequential order as the pharmaceutical items are actually stored on the requesting secondary seller's shelving system (e.g., the secondary seller's 22 request may list the twelfth pharmaceutical item P12 before the first pharmaceutical item P1). Regardless, the computer system 32 reviews the shelving information, the compartment information, and the request, and then automatically generates the Compartment Assignment Plan.

An example Compartment Assignment Plan 210 commensurate with the above, hypothetical shelving system 34A and request, and generated in accordance with the present disclosure, is shown in FIG. 6. In general terms, the Compartment Assignment Plan 210 provides a listing, recipe, or map of what pharmaceutical items are to be loaded in which compartments. The generated Compartment Assignment Plan 210 can be provided in various forms, such as a graphical representation or illustration of the compartments C along with the corresponding, to-be-loaded pharmaceutical items as shown in FIG. 6; a written-only explanation (e.g., "three boxes of 50 mg tablet aspirin are placed in the upper left compartment"); etc. Additional instructions can optionally be provided with, or as an addendum to, the Compartment Assignment Plan that assist the primary distributor's 20 employee(s) in loading of the cart 30. For example, the location or order in which the primary seller 20 maintains pharmaceutical items at the warehouse 24 can be accounted for by the computer system 32, and specific instructions provided that allow the employee to quickly move through the warehouse 24 in filling a request (e.g., the additional instructions can instruct the employee to start at one side of the warehouse 24 and move in a certain path to obtain all of the requested items, with the employee "picking" the requested items and loading the items to the compartments C as specified by the Compartment Assignment Plan). For purposes of the following explanation, the Compartment Assignment Plan 210 schematically illustrates the compartments C (of the selected cart), along with a general representation of the pharmaceutical items to be loaded in each compartment, with the compartments C being generally labeled in accordance with the conventions described above (e.g., the left, upper-most compartment is designated as $C_{1,1}$).

The Compartment Assignment Plan 210 of FIG. 6 directs the primary distributor 20 to load the requested quantity of the first pharmaceutical item P1 in the top left compartment $C_{1,1}$. Under circumstances in which a size/volume of the top left compartment $C_{1,1}$ is not large enough to receive the entire requested quantity of the first pharmaceutical item P1, the Compartment Assignment Plan 210 designates or assigns the second compartment $C_{2,1}$ for loading of additional quantities of the first pharmaceutical item P1. Where necessary, additional, sequential ones of the compartments (i.e., $C_{3,1}$, etc.) can also be designated for loading of the first pharmaceutical item P1. As a point of reference, FIG. 6 reflects the Compartment Assignment Plan 210 as assigning the first three compartments $C_{1,1}$-$C_{3,1}$ for loading of the first pharmaceutical item P1.

The sequentially-next available compartment C (i.e., the $C_{4,1}$) is designated by the Compartment Assignment Plan 210 for loading with the fifth pharmaceutical item P5. Once again, where necessary, additional, sequentially-next compartments (i.e., the fifth compartment $C_{5,1}$) are designated by the Compartment Assignment Plan 210 for loading of the fifth pharmaceutical item P5 sufficient to provide the full quantity requested by the requesting secondary seller 22. The Compartment Assignment Plan 210 follows this same protocol in assigning the twelfth and seventeenth pharmaceutical items P12, P17 to the compartments C in a sequentially-next fashion. In one convention, the sequentially-next protocol entails left-to-right, followed by top-to-bottom (e.g., relative to the Compartment Assignment Plan 210 of FIG. 6, the "sequentially-next" compartment following the last compartment of the first row (i.e., the compartment $C_{5,1}$) is the first compartment of the second row (i.e., the compartment $C_{1,2}$)). The "sequentially-next" compartment following the last compartment of the second row (i.e., the compartment $C_{5,2}$) is the first compartment of the third row (i.e., the compartment $C_{1,3}$); etc. Alternatively, the sequentially-next protocol employed by the computer system 32 in generating a Compartment Assignment Plan can be top-to-bottom followed by left-to-right (i.e., the first compartment of the second row $C_{2,1}$ is deemed to be "sequentially-next" after the first compartment of the first row $C_{1,1}$). The Compartment Assignment Plan 210 of FIG. 6 reflects the designated loading of compartments in meeting the hypothetical request described above.

An ability of the Compartment Assignment Plan to specifically designate two or more of the compartments C for accommodating an entire quantity of a requested pharmaceutical item (e.g., the compartments $C_{1,1}$-$C_{3,1}$ all receive the first pharmaceutical item P1 with the Compartment Assignment Plan 210 of FIG. 6) is a function of the computer system 32 "knowing" the size/volume of each compartment C, as well as a size/volume of individual ones of the requested pharmaceutical item. Thus, for example, the computer system 32 can be programmed to maintain a database of size/volume information for all of the pharmaceutical items maintained in the primary distributor's inventory. Size/volume information for the compartments C of the cart 30 is also stored. By evaluating the pharmaceutical size information and requested quantity of a pharmaceutical item relative to the size/volume of the compartments, the computer system 32 can generate a complete Compartment Assignment Plan. Alternatively, the computer system 32 can be programmed to estimate one or both of the compartment size/volume and the pharmaceutical item size/volume (e.g., the computer system 32 can include a default form factor size for all compartments and/or all pharmaceutical items), and base the compartment assignment determination upon this or these estimates.

Alternatively, the generated Compartment Assignment Plan may not include a pharmaceutical item designation for each individual compartment. Instead, the Compartment Assignment Plan will list the order in which the pharmaceutical items are to be loaded into the compartments, with the person(s) performing the loading operation being instructed or trained as to the sequential "ordering" of the compartments C. For example, and with respect to the example secondary seller request described above, the generated Compartment Assignment Plan will include written and/or illustrated instructions to the effect of "[Quantity Z] of pharmaceutical P1 are loaded first, followed by [Quantity Y] of pharmaceutical item P5, followed by [Quantity X] of pharmaceutical item P12, and followed by [Quantity W] of pharmaceutical item P17." From these instructions, the primary distributor 20 (or, more particularly, an employee of the primary distributor 20) will understand that the first compartment $C_{1,1}$ should be loaded with as much of the first pharmaceutical item P1 as can reasonably be accommodated, with additional quantities (if necessary) of the first pharmaceutical item P1 being loaded into the sequentially-next available compartment (i.e., the compartment $C_{2,1}$). This "natural" loading by the primary distributor 20 will result in final loaded arrangement commensurate with that of FIG. 6.

Returning to FIG. 5, the cart 30 is loaded in accordance with the generated Compartment Assignment Plan at step 222. The loaded cart 30 is then delivered (e.g., over-the-road truck) to the requesting secondary seller 22 (as described in greater detail below) at step 224. Finally, at step 226, the secondary seller 22 unloads the pharmaceutical items directly from the cart 30 and directly onto the secondary seller's shelving system 34.

More particularly, and with cross-reference between FIGS. 2 and 6, an employee of the requesting secondary seller 22 simply maneuvers (e.g., rolls) the loaded cart 30 to the entrance end 52 of the shelving system 34A. Upon reaching the first segment $T_1$, the first pharmaceutical items P1 are unloaded from the first compartment $C_{1,1}$ and placed onto an available space at the corresponding shelving storage regions (i.e., the first or second storage regions 50a or 50b that otherwise are provided by the first and second shelves 40a, 40b of the first segment $T_1$). The second and third compartments $C_{2,1}$ and $C_{3,1}$ are similarly unloaded to the storage region(s) 50a or 50b. The cart 30 is then maneuvered or wheeled to the second segment $T_2$, and the fifth pharmaceutical items P5 are unloaded from the fourth and fifth compartments $C_{4,1}$ and $C_{5,1}$ and placed onto the corresponding shelving storage regions (i.e., the storage regions 50g or 50h of the second segment $T_2$). This same process is repeated in unloading the twelfth pharmaceutical items P12 from the sixth compartment $C_{1,2}$ to the storage region 50n of the fourth segment $T_4$, and the seventeenth pharmaceutical items P17 from the seventh-ninth compartments $C_{2,2}$-$C_{2,4}$ to the storage region 50q of the fifth segment $T_5$. Notably, because the pharmaceutical items $P_1$, $P_5$, $P_{12}$, and $P_{17}$ have been ordered on the cart 30 in sequentially-next compartment(s) C corresponding with the order in which the pharmaceutical items P1, P5, P12, and P17 are stored along the secondary seller's shelving system 34A, the secondary seller's employee will quickly recognize which compartment is to be unloaded, and is not required to repeatedly move the cart 30 back-and-forth relative to the shelving system 34A. Rather, the cart 30 is simply moved from the entrance end 52 to the exit end 54, with pharmaceutical items to be unloaded being presented by the cart 30 to the employee in the proper order.

Figure 7:
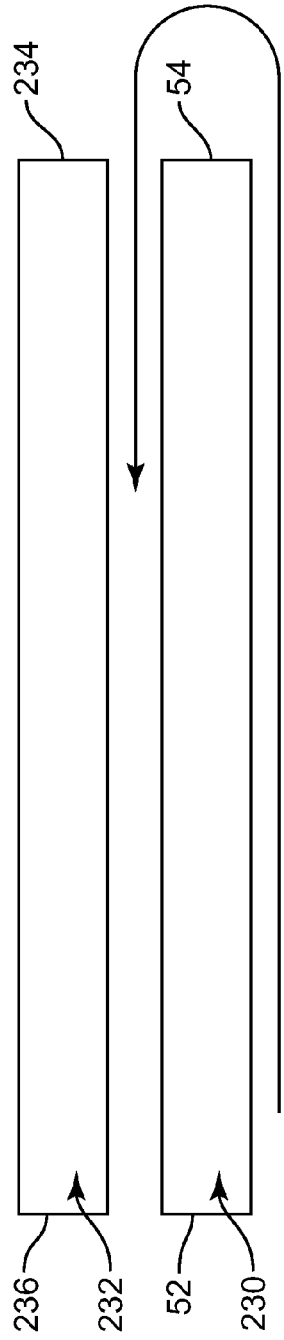
FIGS. 7A and 7B are simplified views of an example shelving system and corresponding pharmaceutical storage designations of a secondary seller of the distribution system of FIG. 1.

While the Compartment Assignment Plan described above relates to a secondary seller having only a single line shelving system 34A, the systems and methods of the present disclosure are equally applicable to multiple line shelving systems 34. Modifying the above example, and with reference to FIGS. 7A and 7B, in addition to the line of shelves described above (illustrated generally in FIG. 7A as the line of shelves 230), it is assumed for purposes of this one example that the shelving system 34C of the requesting secondary seller further includes a second line of shelves 232 as shown. The second line of shelves 232 maintains pharmaceutical items P21-P35 as shown in FIG. 7B. Based upon an expected travel path (represented by an arrow in FIG. 7A) in which the requesting secondary seller's 22 employee will first move along and unload pharmaceutical items to the first line of shelves 230, beginning at the entrance end 52 and ending at the exit end 54, a most convenient travel pattern subsequently entails moving from the exit end 54 of the first line of shelves 230 to an exit end 234 of the second line of shelves 232. Where additional lines of shelves are provided, this same travel path is repeated, akin to a serpentine pattern. The corresponding Compartment Assignment Plan generated in accordance with some embodiments of the present disclosure accounts for this expected travel path in assigning requested pharmaceutical items to remaining ones of the compartments C.

For example, and continuing with the above hypothetical, where the request of the requesting secondary seller 22 further includes a quantity of the twenty-fifth pharmaceutical item P25 and a quantity of the thirty-second pharmaceutical item P32, the computer system 32 (FIG. 1) will generate a Compartment Assignment Plan that assigns the sequentially-next available compartment (sequentially after the last compartment C to which the seventeenth pharmaceutical item P17 was assigned) in FIG. 6 for loading of the thirty-second pharmaceutical item P32. FIG. 8 illustrates a corresponding Compartment Assignment Plan 240, designating the tenth-twelfth compartments $C_{5,2}$-$C_{2,3}$ for loading of the thirty-second pharmaceutical item P32. The twenty-fifth pharmaceutical item P25 is assigned to a sequentially-next available compartment(s) as necessary (i.e., the Compartment Assignment Plan 240 of FIG. 8 reflects the twenty-fifth pharmaceutical items P25 being assigned to the thirteenth compartment $C_{3,3}$).

Assuming the cart 30 is loaded in accordance with the Compartment Assignment Plan 240 and delivered to the requesting secondary seller 22, an employee of the requesting secondary seller 22 unloads the pharmaceutical items P1, P5, P12, and P17 to the first line of shelves 230 as described above. Following unloading of the seventeenth pharmaceutical items P17, the requesting secondary seller's employee moves the cart 30 from the exit end 54 of the first line of shelves 230 to the exit end 234 of the second line of shelves 232, and toward the storage region(s) at which the thirty-second pharmaceutical item P32 is located. The thirty-second pharmaceutical items P32 are then unloaded from the corresponding compartments $C_{5,2}$-$C_{2,3}$ to the corresponding shelving storage region(s). Notably, the requesting secondary seller's employee will quickly recognize which compartment is to be unloaded next (following unloading of the seventeenth pharmaceutical items P17) as all compartments C "before" the tenth compartment $C_{5,2}$ will be empty. Finally, the cart 30 is further moved along the second line of shelves 232 (toward an entrance end 236) until the storage region(s) of the twenty-fifth pharmaceutical items P25 are reached. The twenty-fifth pharmaceutical items P25 are then unloaded from the compartment $C_{3,3}$ to the corresponding shelf storage region.

The Compartment Assignment Plans described above are but two, non-limiting examples. The systems and methods of the present disclosure can create virtually any Compartment Assignment Plan commensurate with the secondary seller's shelving system/item arrangement and requested pharmaceutical items. Further, the Compartment Assignment Plan can include pharmaceutical item/compartment designations for two or more carts (e.g., to fill a large request, two or more carts may be required; under these circumstances, the Compartment Assignment Plan will dictate not only the pharmaceutical items to be placed in the compartments of each cart, but also the order in which the carts should be unloaded). Also, the Compartment Assignment Plan can account for a "back-to-back" shelving system (e.g., the shelving system 34B of FIG. 3B) in which a most-convenient unloading pattern entails moving the cart along an aisle (between two lines of shelves) in a single direction while unloading pharmaceutical items to both lines of shelves from sequential compartments. For example, the Compartment Assignment Plan may entail loading of a first compartment with a quantity of pharmaceutical items to be unloaded at the first line of shelves, and loading of a sequentially-next compartment with a quantity of pharmaceutical items to be unloaded at the second line of shelves. Along these same lines, the Compartment Assignment Plan can relate to a cart having compartments available at both sides. Under these circumstances, for example, the Compartment Assignment Plan can assign pharmaceutical items to be unloaded to the first line of shelves to compartments of the first side, and pharmaceutical items to be unloaded to the second line of shelves to the second side.

In more basic terms, by referencing the shelving information of a particular secondary seller, and correlating this information with the arrangement of compartments provided with a designated cart, pharmaceutical items can be provided to the secondary seller in a manner promoting optimal unloading to the secondary seller's shelves. Further, by eliminating the use of conventional totes, the secondary seller is not required to remove, sort, and kit products from a plethora of totes, thus saving valuable time.

Figure 9B:
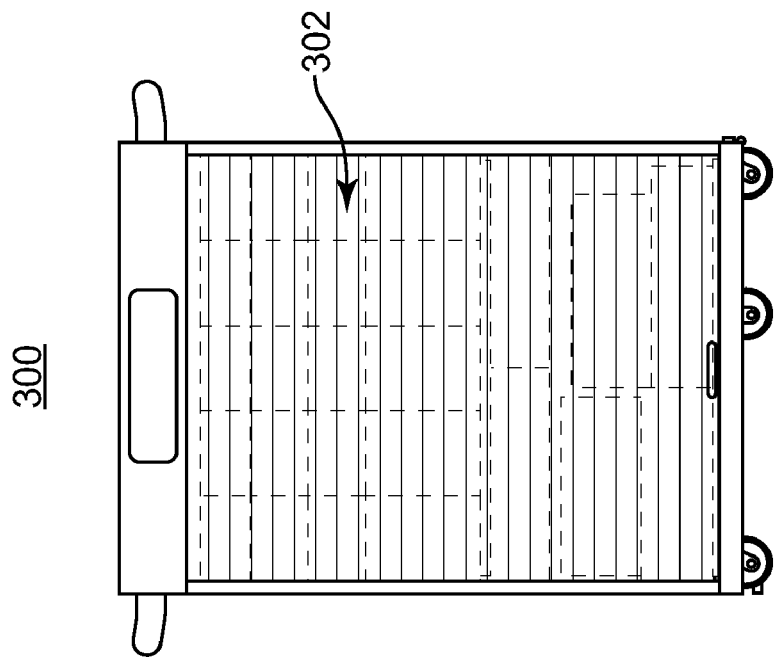
FIGS. 9A and 9B are side views of another cart useful with the distribution systems and methods of the present disclosure.
Figure 9A:
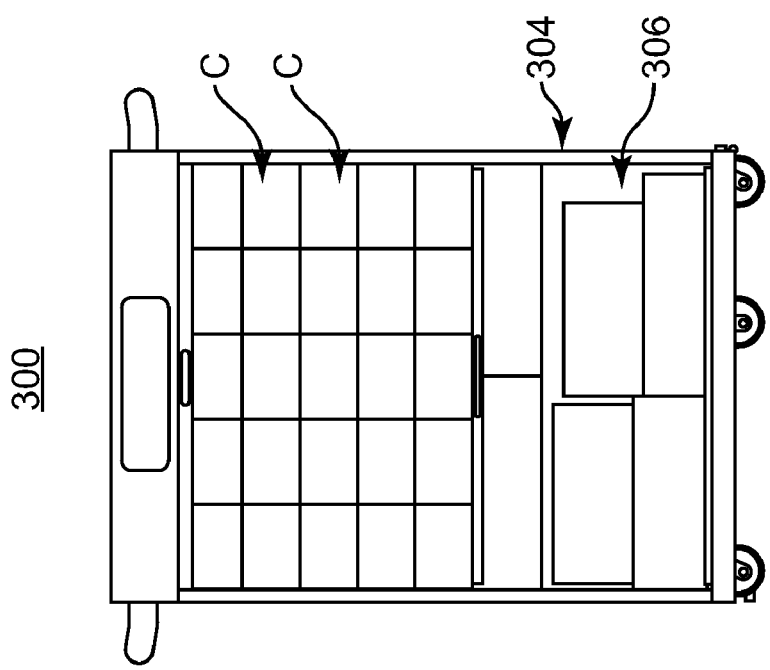

In some embodiments, the cart useful with the present disclosure is configured for direct, over-the-road delivery to the requesting secondary seller. In this regard, and with reference to FIGS. 9A and 9B, in some embodiments, a cart 300 is provided with not only the compartments C described above, but also means for selectively closing the compartments C in a manner facilitating safe transport by truck. For example, a door 302 can be provided that is movably retained by the cart's frame 304 for collectively opening (FIG. 9A) and closing (FIG. (9B) one or all of the compartments C. Alternatively, a separate door can be provided for each individual compartment. Other optional features, such as a storage area 306, are further reflected in FIG. 9A.

Although the present disclosure has been described with reference to preferred embodiments, workers skilled in the art will recognize that changes can be made in form and detail without departing from the spirit and scope of the present disclosure. For example, while the systems and methods have been described as employing a computer system that generates the Compartment Assignment Plans, in other embodiments, the manner/order in which the compartments are to be loaded is manually determined. Further, the systems and methods can be employed by a pharmaceutical manufacturer in delivering items to a primary distributor; and/or by a national logistics center (NLC) in delivering items to an affiliated distribution center. Under these circumstances, the cart(s) can be loaded pursuant to a Compartment Assignment Plan that relates to the shelving arrangement of the primary distributor, or to the shelving arrangement of a secondary seller customer of the primary distributor (e.g., the manufacturer or NLC can "build" a cart(s) for filling a particular secondary seller's request). Even further, the primary distributor (or manufacturer or NLC) can employ the systems and methods of the present disclosure to generate a partially or completely filled, "standard" cart for a particular end user. For example, a particular secondary seller may regularly order a quantity of pharmaceutical items A and B. In recognition of this, the primary distributor can partially fill a cart with a certain quantity of items A and B, and set the so-loaded cart to the side until an actual order is received from the secondary seller. Once the order is received, the Compartment Assignment Plan is generated, with items A and B assigned to the compartment(s) already loaded with the items A and B. The primary distributor's employee then fills a remainder of the partially loaded cart with the remaining items requested, thus saving time.

What is claimed is:

1. A computer-assisted method of distributing pharmaceutical items from a primary distributor to a secondary seller of pharmaceuticals, the computer comprising a processor, the method comprising:

maintaining an inventory of pharmaceutical items at the primary distributor;

receiving a request from the secondary seller to the primary distributor for a plurality of different pharmaceutical items;

reviewing, via the processor, shelving information indicative of a sequential arrangement of pharmaceutical items along a shelving system maintained by the secondary seller;

providing a mobile cart having a plurality of compartments;

designating a sequential order to the plurality of compartments;

creating a compartment assignment plan based upon the request, the shelving information, and the designated sequential order of compartments, wherein the compartment assignment plan assigns all of the requested pharmaceutical items to individual compartments in an order corresponding with the sequential arrangement of the requested pharmaceutical items along the shelving system;

loading the compartments with the requested pharmaceutical items from the inventory of the primary distributor in accordance with the compartment assignment plan; and delivering the loaded cart to the secondary seller.

2. The method of claim 1, wherein the mobile cart is not an individual pharmaceutical item-containing tote.

3. The method of claim 1, wherein the request includes a request for a quantity of a first pharmaceutical item, a quantity of a second pharmaceutical item, and a quantity of a third pharmaceutical item, and further wherein the sequential arrangement of pharmaceutical items along the shelving system includes the first pharmaceutical item sequentially located between the second pharmaceutical item and the third pharmaceutical item, and even further wherein creating a compartment assignment plan includes assigning the first pharmaceutical item to a compartment sequentially located between a compartment assigned for the second pharmaceutical item and a compartment assigned for the third pharmaceutical item.

4. The method of claim 1, wherein reviewing shelving information includes electronically receiving the shelving information by the primary distributor from the secondary seller.

5. The method of claim 1, wherein reviewing shelving information includes the primary distributor maintaining an electronic database of shelving information for a plurality of different secondary sellers.

6. The method of claim 1, wherein the shelving system of the secondary seller includes a first line of shelves and a second line of shelves each extending between first and second ends, respectively, and further wherein the shelving information indicates a sequential order of all pharmaceutical items maintained along the first line, beginning with the pharmaceutical item maintained at the first end of the first line and ending with the pharmaceutical item maintained at the second end of the first line.

7. The method of claim 6, wherein the shelving information includes a sequential order of all pharmaceutical items maintained along the second line, beginning with the pharmaceutical item maintained at the first end of the second line and ending with the pharmaceutical item maintained at the second end of the second line.

8. The method of claim 7, wherein the shelving information includes an indication of an expected travel path relating to whether the mobile cart will be moved from the second end of the first line to the first end of the second line when the cart is unloaded at the secondary seller.

9. The method of claim 7, wherein the compartment assignment plan sequentially assigns a pharmaceutical item to be located on the first line of shelves to a compartment that is sequentially before a compartment assigned to contain the pharmaceutical item to be located on the second line of shelves.

10. The method of claim 1, wherein the compartments are arranged in an array including a top row of compartments and a second row of compartments immediately below the top row, each of the rows of compartments including a first compartment at a left side of the row and a last compartment at a right side of the row, and further wherein designating the sequential row of compartments includes:
designating the first compartment of the first row as being compartment $C_1$;
designating the last compartment of the first row as being compartment $C_x$; and
designating the first compartment of the second row as being compartment $C_{x+1}$.

11. The method of claim 1, wherein the compartment assignment plan is electronically created.

12. The method of claim 1, wherein creating the compartment assignment plan includes printing a paper copy of the compartment assignment plan.

13. The method of claim 1, further comprising:
closing each of the compartments prior to delivering the loaded cart to the secondary seller.

14. The method of claim 1, further comprising:
unloading the pharmaceutical items from the compartments to the shelving system while moving the cart along the shelving system in a single direction.

15. The method of claim 14, wherein unloading the loaded pharmaceutical items includes:
unloading the compartments sequentially.

16. The method of claim 1, wherein the compartment assignment plan is a first compartment assignment plan, the method further comprising:
receiving a second request from the secondary seller for pharmaceutical items; and
creating a second compartment assignment plan based upon the second request, the shelving information, and the designated sequential order of compartments;
wherein the second compartment assignment plan differs from the first compartment assignment plan; and
loading a second cart in accordance with the second compartment assignment plan.

17. The method of claim 1, wherein the compartment assignment plan is a first compartment assignment plan, the method further comprising:
receiving a second request from a second secondary seller to the primary distributor for different pharmaceutical items;
receiving second shelving information indicative of a sequential arrangement of pharmaceutical items along a shelving system maintained by the second secondary seller;
creating a second compartment assignment plan based upon the second request, the second shelving information and the designated sequential order of compartments;
wherein the second compartment assignment plan differs from the first compartment assignment plan; and
loading a second cart in accordance with the second compartment assignment plan.

18. The method of claim 1, wherein the cart defines a first side and a second side, the plurality of compartments including a first set of compartments accessible via the first side and a second set of compartments accessible via the second side, and further wherein the designated sequential order of compartments includes:
designating the first compartment of the first set as compartment $C_1$;
designating the last compartment of the first set as compartment $C_n$; and
designating the first compartment of the second set as compartment $C_{n+1}$.

19. The method of claim 1, wherein the cart defines a first side and a second side, the plurality of compartments including a first set of compartments accessible via the first side and a second set of compartments accessible via the second side, and further wherein the shelving system includes a first line of shelves and a second line of shelves, the first and second lines facing one another and separated by an aisle, and even further wherein creating a compartment assignment plan includes:
assigning requested pharmaceutical items to be located along the first line of
shelves to the first set of compartments; and
assigning requested pharmaceutical items to be located along the second line of shelves to the second set of compartments.

20. The method of claim 1, wherein creating a compartment assignment plan includes:
determining that a second cart is required to deliver all the requested pharmaceutical items to the secondary seller;
generating a first cart compartment assignment plan that assigns pharmaceutical items to all of the compartments of the first cart; and
generating a second cart compartment assignment plan that assigns requested pharmaceutical items not otherwise assigned by the first cart compartment assignment plan to compartments of the second cart.

21. The method of claim 1, wherein the pharmaceutical item request includes a request for a first pharmaceutical item in a first format and a request for the first pharmaceutical item in a second format, and further wherein the sequential arrangement of pharmaceutical items along the shelving system includes the first format of the first pharmaceutical item being sequentially before the second format of the first pharmaceutical item, even further wherein creating a compartment assignment plan includes:

assigning the first pharmaceutical item in the first format to a compartment sequentially arranged before a compartment to which the first pharmaceutical item in the second format is assigned.

22. The method of claim 1, wherein the reviewed shelving information indicates sequential arrangement of pharmaceutical items along the shelving system both vertically and horizontally relative to one another.

23. The method of claim 1, wherein the secondary seller is a retail pharmacy.

24. A system for warehousing and distributing pharmaceutical items, the system comprising:

a warehouse maintaining an inventory of a plurality of pharmaceutical items; at least one mobile cart having a plurality of compartments; and a computer programmed to:
  receive a request from a secondary seller for different pharmaceutical items,
  review shelving information indicative of a sequential arrangement of pharmaceutical items along a shelving system maintained by the secondary seller,
  designate a sequential order to the plurality of compartments of the at least one cart,
  create a compartment assignment plan based upon the request, the shelving information, and the designated sequential order of compartments, wherein the compartment assignment plan assigns all of the requested pharmaceutical items to individual compartments in an order corresponding with the sequential arrangement of the shelving system;
wherein upon creation of the compartment assignment plan, the system promotes loading of the cart with the requested pharmaceutical items by reference to the compartment assignment plan for delivery to the secondary seller.

* * * * *